United States Patent
Bakken

(10) Patent No.: US 11,596,317 B2
(45) Date of Patent: Mar. 7, 2023

(54) FLUID PRESSURE SENSOR PROTECTION

(71) Applicant: ACIST Medical Systems, Inc., Eden Prairie, MN (US)

(72) Inventor: Matthew James Russell Bakken, Bloomington, MN (US)

(73) Assignee: ACIST Medical Systems, Inc., Eden Prairie, MN (US)

(*) Notice: Subject to any disclaimer, the term of this patent is extended or adjusted under 35 U.S.C. 154(b) by 797 days.

(21) Appl. No.: 16/670,402

(22) Filed: Oct. 31, 2019

(65) Prior Publication Data
US 2020/0129079 A1    Apr. 30, 2020

Related U.S. Application Data

(60) Provisional application No. 62/753,472, filed on Oct. 31, 2018.

(51) Int. Cl.
| | |
|---|---|
| *A61B 5/021* | (2006.01) |
| *A61B 5/0235* | (2006.01) |
| *G01L 19/14* | (2006.01) |

(52) U.S. Cl.
CPC ........ *A61B 5/02141* (2013.01); *A61B 5/0235* (2013.01); *G01L 19/142* (2013.01); *A61B 2562/0247* (2013.01); *G01L 19/149* (2013.01)

(58) Field of Classification Search
CPC .............. A61B 5/02141; A61B 5/0235; A61B 2562/0247; G01L 19/142; G01L 19/149; A61M 5/48; A61M 5/16854
See application file for complete search history.

(56) References Cited

U.S. PATENT DOCUMENTS

| | | |
|---|---|---|
| 3,863,504 A | 2/1975 | Borsanyi |
| 3,868,844 A | 3/1975 | Klein |
| (Continued) | | |

FOREIGN PATENT DOCUMENTS

| | | |
|---|---|---|
| CN | 1913825 A | 2/2007 |
| CN | 101184977 A | 5/2008 |
| (Continued) | | |

OTHER PUBLICATIONS

Merit Sensor BP Series Data Sheet (Sep. 19, 2018), 4 pgs.
(Continued)

*Primary Examiner* — Gary Jackson
*Assistant Examiner* — Sebastian X Lukjan
(74) *Attorney, Agent, or Firm* — Crowell & Moring LLP

(57) ABSTRACT

Embodiments for protecting low-pressure blood pressure sensors in high-pressure fluid flow applications by equalizing pressure on both sides of a pressure sensor's diaphragm during high pressure are disclosed. A sensor protection device may include a pressure sensor assembly, a housing, and a plunger assembly. During low pressure, fluid in the primary flow path can flow through the housing, transferring its pressure to a first side of the diaphragm; the plunger assembly can prevent fluid flow into a secondary flow path in the housing, transferring atmospheric pressure to a second side of the diaphragm. During high pressure, fluid can still flow through the primary flow path, and the plunger assembly may now allow fluid flow into the secondary flow path, transferring pressure from the same fluid to the second side of the diaphragm to equal pressure across the diaphragm. The plunger assembly may automatically transition between low- and high-pressure configurations.

20 Claims, 8 Drawing Sheets

(56) References Cited

U.S. PATENT DOCUMENTS

| | | | |
|---|---|---|---|
| 4,226,124 A | 10/1980 | Kersten | |
| 4,227,420 A | 10/1980 | Lamadrid | |
| 4,274,423 A | 6/1981 | Mizuno et al. | |
| 4,314,480 A | 2/1982 | Becker | |
| 4,375,182 A | 3/1983 | Zavoda | |
| 4,722,348 A | 2/1988 | Ligtenberg et al. | |
| 4,959,050 A | 9/1990 | Bobo, Jr. | |
| 5,024,099 A | 6/1991 | Lee | |
| 5,031,460 A | 7/1991 | Kanenobu et al. | |
| 5,105,820 A | 4/1992 | Moriuchi et al. | |
| 5,280,786 A | 1/1994 | Wlodarczyk et al. | |
| 5,335,584 A | 8/1994 | Baird | |
| 5,346,470 A | 9/1994 | Hobbs et al. | |
| 5,449,003 A | 9/1995 | Sugimura | |
| 5,808,203 A | 9/1998 | Nolan, Jr. et al. | |
| 6,077,443 A | 6/2000 | Goldau | |
| 6,371,942 B1 | 4/2002 | Schwartz et al. | |
| 6,568,241 B2 | 5/2003 | Cole | |
| 7,094,216 B2 | 8/2006 | Trombley, III et al. | |
| 7,163,385 B2 | 1/2007 | Gharib et al. | |
| 7,373,826 B2 | 5/2008 | Weber et al. | |
| 7,389,788 B2 | 6/2008 | Wilson et al. | |
| 7,610,936 B2 | 11/2009 | Spohn et al. | |
| 7,617,837 B2 | 11/2009 | Wilson et al. | |
| 7,722,557 B2 | 5/2010 | Sano et al. | |
| 7,905,246 B2 | 3/2011 | Wilson et al. | |
| 9,427,515 B1 * | 8/2016 | Nystrom | A61M 5/007 |
| 2003/0122095 A1 | 7/2003 | Wilson et al. | |
| 2004/0010229 A1 | 1/2004 | Houde et al. | |
| 2005/0120773 A1 | 6/2005 | Ohl et al. | |
| 2006/0180202 A1 | 8/2006 | Wilson et al. | |
| 2007/0179422 A1 | 8/2007 | Schnell et al. | |
| 2008/0058720 A1 | 3/2008 | Spohn et al. | |
| 2008/0154214 A1 | 6/2008 | Spohn et al. | |
| 2009/0149743 A1 | 6/2009 | Barron et al. | |
| 2010/0228136 A1 | 9/2010 | Keel et al. | |
| 2010/0234698 A1 | 9/2010 | Manstrom et al. | |
| 2010/0241008 A1 | 9/2010 | Belleville et al. | |
| 2010/0249587 A1 | 9/2010 | Duchon et al. | |
| 2010/0268098 A1 | 10/2010 | Ito et al. | |
| 2011/0009800 A1 | 1/2011 | Dam et al. | |
| 2013/0255390 A1 | 10/2013 | Riley et al. | |
| 2014/0052009 A1 | 2/2014 | Nystrom et al. | |

FOREIGN PATENT DOCUMENTS

| | | |
|---|---|---|
| CN | 101421602 A | 4/2009 |
| DE | 20019067 U1 | 2/2001 |
| EP | 1213035 A1 | 6/2002 |
| EP | 1655044 A2 | 5/2006 |
| JP | 63059452 A | 3/1988 |
| JP | 08117332 A | 5/1996 |
| WO | 9854555 A1 | 12/1998 |
| WO | 0247751 A2 | 6/2002 |
| WO | 03050491 A2 | 6/2003 |
| WO | 2004061399 A2 | 7/2004 |
| WO | 2007050553 A1 | 5/2007 |
| WO | 2010030882 A1 | 3/2010 |
| WO | 2011002744 A1 | 1/2011 |
| WO | 2011113643 A1 | 9/2011 |
| WO | 2012151542 A2 | 11/2012 |
| WO | 2015061723 A2 | 4/2015 |
| WO | 2017018974 A1 | 2/2017 |

OTHER PUBLICATIONS

Conrad, "Pressure-Flow Relationships in Collapsible Tubes," IEEE Transactions on Biomedical Engineering, vol. BME-16, No. 4, 1969, p. 284.

Force Sensors Line Guide, Honeywell International, Inc., Golden Valley, Minnesota, Jun. 2009, 3 pages.

Kleinman et al., "Equivalence of Fast Flush and Square Wave Testing of Blood Pressure Monitoring Systems," Journal of Clinical Monitoring, vol. 12, 1996, pp. 149-154.

Miller et al., "Cardiovascular Monitoring," Miller's Anesthesia, Churchill Livingstone/Elsevier, 7th Edition, Chpt. 40, 2010, p. 1278.

National Instruments, "Signal Generator Fundamentals," Retrieved from the Internet <http://zone.ni.zone/devzone/cda/tut/p/id/4089>, 2006.

Smiths Medical International Ltd, Logical—The Innovative Pressure Transducer System; Literature No. LIT/PV2588; Hythe, Kent, United Kingdom, 2006, 2 pages.

International Patent Application No. PCT/US2019/059144, International Search Report and Written Opinion dated Feb. 13, 2020, 14 pages.

* cited by examiner

FLUID PRESSURE SENSOR PROTECTION

CROSS-REFERENCE TO RELATED APPLICATIONS

This application claims the benefit of U.S. Provisional Application No. 62/753,472, filed Oct. 31, 2018, the contents of which are incorporated herein by reference.

TECHNICAL FIELD

This disclosure relates generally to the field of medical technology and, more particularly, to devices, systems, and methods for protecting low-pressure pressure sensors in high-pressure fluid flow applications.

BACKGROUND

Conventional pressure sensors designed to work at low pressures may fail in high-pressure applications. For example, some low-pressure pressure sensors can perform pressure measurements up to 5.8 psi and have an overpressure rating of around 125 psi. These pressure sensors will fail and rupture at pressures exceeding the overpressure rating. Such high pressures are generated in fluid lines in a variety of applications including, for instance, angiographic contrast injection procedures.

Low-pressure pressure sensors exposed to the pressures of high-pressure angiographic contrast injections are likely to fail. Precise pressure measurements are desirable during angiography procedures (e.g., to measure blood pressure) and are typically performed using a pressure sensor for measuring pressures in a fluid line. An angiographic contrast injection procedure may utilize a number of components to introduce a fluid, such as a contrast medium, intravenously to a patient through the fluid line at high pressures. For example, a contrast media powered injection system may include a source of contrast media coupled to a pressurizing unit from which contrast is injected through a fluid injection line, to facilitate imaging during certain medical procedures. Contrast media is typically injected at high pressures, up to 1200 psi in some instances. Conventional low-pressure pressure sensors will fail if exposed to these pressures.

Using conventional low-pressure sensors in applications such as angiographic contrast injection procedures presents several challenges. Diaphragms of low-pressure pressure sensors will rupture at angiographic contrast injection pressures and become unusable. On the other hand, diaphragms of high-pressure pressure sensors designed to withstand angiographic contrast injection pressures are typically not sensitive enough to take precise blood pressure measurements during angiography contrast injection procedures. Previous solutions required additional components separate from the fluid injection line to measure blood pressure in such procedures.

SUMMARY

Embodiments disclosed in this document protect conventional, low-pressure blood pressure sensors during high-pressure applications by equalizing pressure on both sides of the pressure sensor's diaphragm, thereby preventing the diaphragm from rupturing. The sensor protection device can, depending on pressure and fluid flow, transition between configurations to affect the pressure differential across the diaphragm. Many instances of the device may do so by itself with little or no direct operator intervention.

During low pressure, the device can create a pressure differential across the diaphragm to measure pressure. A first side of a sensor diaphragm may be exposed to pressure from fluid in a primary flow path. The sensor protection device can then ensure a second opposed side of the sensor diaphragm is exposed to atmospheric pressure, thereby creating a pressure differential across the sensor diaphragm. This pressure differential may be used to establish fluid pressure.

During high-pressure operations, the device may create equilibrium across the diaphragm. The first side of the sensor diaphragm may remain exposed to pressure from fluid in the primary flow path. The increased pressure in the primary flow path, however, may open a valve in the sensor protection device to allow fluid from the primary flow path into a secondary flow path. The sensor protection device may ensure a second side of the sensor diaphragm is exposed to pressure from fluid in the secondary flow path (instead of atmospheric pressure). In such instances, pressure from fluid in the primary flow path may equal pressure from fluid in the secondary flow path and, thus, no pressure differential occurs across the sensor diaphragm.

The sensor protection device can transition from the high-pressure configuration to the low-pressure configuration. The first side of the sensor diaphragm may remain exposed to pressure from fluid in the primary flow path. Decreased pressure in the primary flow path may allow the valve in the sensor protection device to close, thereby preventing fluid from the primary flow path from entering the secondary flow path. The sensor protection device can ensure that the second side of the sensor diaphragm is again exposed to atmospheric pressure.

Some examples include a sensor protection device. The sensor protection device can include a pressure sensor assembly, a sensor protection housing, and a plunger assembly. The pressure sensor assembly may include a diaphragm with first and second sides and a pressure sensor housing that houses the diaphragm. The pressure sensor housing may include a first sensor port configured to enable fluid to press against the first side of the diaphragm and a second sensor port configured to enable fluid to press against the second side of the diaphragm. The sensor protection housing can include an inlet, an outlet, a sensor chamber that houses the pressure sensor assembly, a primary flow path from the inlet to the outlet, and a secondary flow path. In many embodiments, the sensor chamber includes a first chamber port aligned with the first sensor port and a second chamber port aligned with the second sensor port. The primary flow path may enable fluid to flow through the first chamber port and the first sensor port. The secondary flow path may enable fluid to flow through the second chamber port and the second sensor port. The plunger assembly is often positioned in the secondary flow path. In many embodiments, the plunger assembly includes a plunger and an axial biasing member. The axial biasing member may be configured to adjust the position of the plunger. For example, the axial biasing member can be configured to position the plunger in a plunger closed position when a pressure of fluid within the sensor protection housing is below a predetermined value. The axial biasing member may also be configured to position the plunger in a plunger open position when the pressure of fluid within the sensor protection housing is above the predetermined value. The plunger may prevent fluid from flowing through the second chamber port and the second sensor port when in the plunger closed position. The plunger may be permit fluid to flow through the second chamber port and the second sensor port when in the plunger open position.

Some examples include a method of protecting a pressure sensor. One step of the method can involve providing a sensor protection housing that includes an inlet, an outlet, a sensor chamber that includes a first chamber port and a second chamber port, a primary flow path from the inlet to the outlet, and a secondary flow path. One step of the method can include providing a plunger assembly positioned in the secondary flow path of the sensor protection housing. The plunger assembly may include a plunger and an axial biasing member. One step of the method may include inserting a pressure sensor assembly into the sensor chamber of the sensor protection housing. The pressure sensor assembly can comprise a diaphragm with first and second sides and a pressure sensor housing. In some instances, the pressure sensor housing houses the diaphragm. In some instances, the pressure sensor housing includes a first sensor port configured to enable fluid to press against the first side of the diaphragm and a second sensor port configured to enable fluid to press against the second side of the diaphragm. Inserting the pressure sensor assembly into the sensor chamber may include aligning the first sensor port with the first chamber port and aligning the second sensor port with the second chamber port. One step of the method may include flowing fluid into the sensor protection housing through the inlet at a fluid pressure. Fluid may flow along the primary flow path and out the outlet and through the first chamber port and the first sensor port. Fluid may flow along the secondary flow path through the second chamber port and the second sensor port if the fluid pressure is above a predetermined value. The plunger may prevent fluid from flowing along the secondary flow path through the second chamber port and the second sensor port if the fluid pressure is below the predetermined value.

Some examples include a sensor protection device. The sensor protection device may include a sensor protection housing and a plunger assembly. The sensor protection housing can include an inlet, an outlet, a sensor chamber, a primary flow path from the inlet to the outlet, and a secondary flow path. The sensor chamber can include first and second chamber ports. In many instances, the sensor chamber can be configured to house a pressure sensor assembly. The pressure sensor assembly can include a diaphragm with first and second sides. The pressure sensor assembly can include a pressure sensor housing that houses the diaphragm. The pressure sensor housing may include a first sensor port configured to enable fluid to press against the first side of the diaphragm and a second sensor port configured to enable fluid to press against the second side of the diaphragm. The first chamber port may be configured to be aligned with the first sensor port. The second chamber port may be configured to be aligned with the second sensor port. The primary flow path can enable fluid to flow through the first chamber port and the first sensor port. The secondary flow path can enable fluid to flow through the second chamber port and the second sensor port. The plunger assembly may be positioned in the secondary flow path. In many examples, the plunger assembly includes a plunger and an axial biasing member. The axial biasing member may be configured to position the plunger in a plunger closed position when a pressure of fluid within the sensor protection housing is below a predetermined value. The axial biasing member may be configured to position the plunger in a plunger open position when the pressure of fluid within the sensor protection housing is above the predetermined value. The plunger may prevent fluid from flowing through the second chamber port and the second sensor port when in the plunger closed position. The plunger may permit fluid to flow through the second chamber port and the second sensor port when in the plunger open position.

Various examples may have one or more of the following features. The sensor protection housing may be composed of first and second complementary segments. Inserting the pressure sensor assembly into the sensor chamber of the sensor protection housing may include mating the first and second complementary segments together by one or more mating sections. In some examples, the first complementary segment includes the inlet and the secondary flow path. In some examples, the second complementary segment includes the outlet. The sensor chamber and the primary flow path may be formed between the one or more mating sections. In some examples, fluid pressed against the first side of the diaphragm and fluid pressed against the second side of the diaphragm are at equal pressure when the fluid pressure is above the predetermined value. In some examples, the second side of the diaphragm is exposed to atmospheric pressure when the fluid pressure is below the predetermined value. In some examples the predetermined value is a value between 60 psi and 1,000 psi (e.g., between 500 psi and 700 psi). The pressure sensor housing may include a first transfer medium reservoir positioned over the first sensor port and a second transfer medium reservoir positioned over the second sensor port. The first transfer medium reservoir can be filled with a first transfer medium to translate pressure from the fluid within the sensor protection housing to the first side of the diaphragm. The second transfer medium reservoir can be filled with a second transfer medium to translate pressure from the fluid within the sensor protection housing to the second side of the diaphragm. In some examples, the first transfer medium and the second transfer medium each comprise fluorosilicone gel. In some examples, the plunger comprises molded elastomer or vulcanized rubber product or vulcanized synthetic rubber. In many such examples, the plunger seals the secondary flow path to prevent fluid from flowing past the plunger. The axial biasing member may include a compression spring.

Using a sensor protection device as disclosed herein can provide several advantages. Such a device can "automatically" switch between low-pressure and high-pressure configurations by itself or with little or no direct operator intervention. Further, the sensor protection device may be positioned in-line with the injection fluid line, eliminating the need for separate components. Further, accurate blood pressure measurements can be obtained during portions of angiographic procedures other than the high-pressure contrast media injection.

The details of one or more examples are set forth in the accompanying drawings and the description below. Other features, objects, and advantages will be apparent from the description and drawings.

BRIEF DESCRIPTION OF DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements.

DETAILED DESCRIPTION

The following detailed description is exemplary in nature and provides some practical illustrations and examples. Those skilled in the art will recognize that many of the noted examples have a variety of suitable alternatives. A number of various exemplary sensor protection systems, devices, and techniques are disclosed herein using the description provided as follows in addition to the accompanying drawings. Each of the systems, devices, and techniques disclosed herein can be employed independently or in combination with one or more (e.g., all) of the other systems, devices, and techniques disclosed herein.

Figure 1:
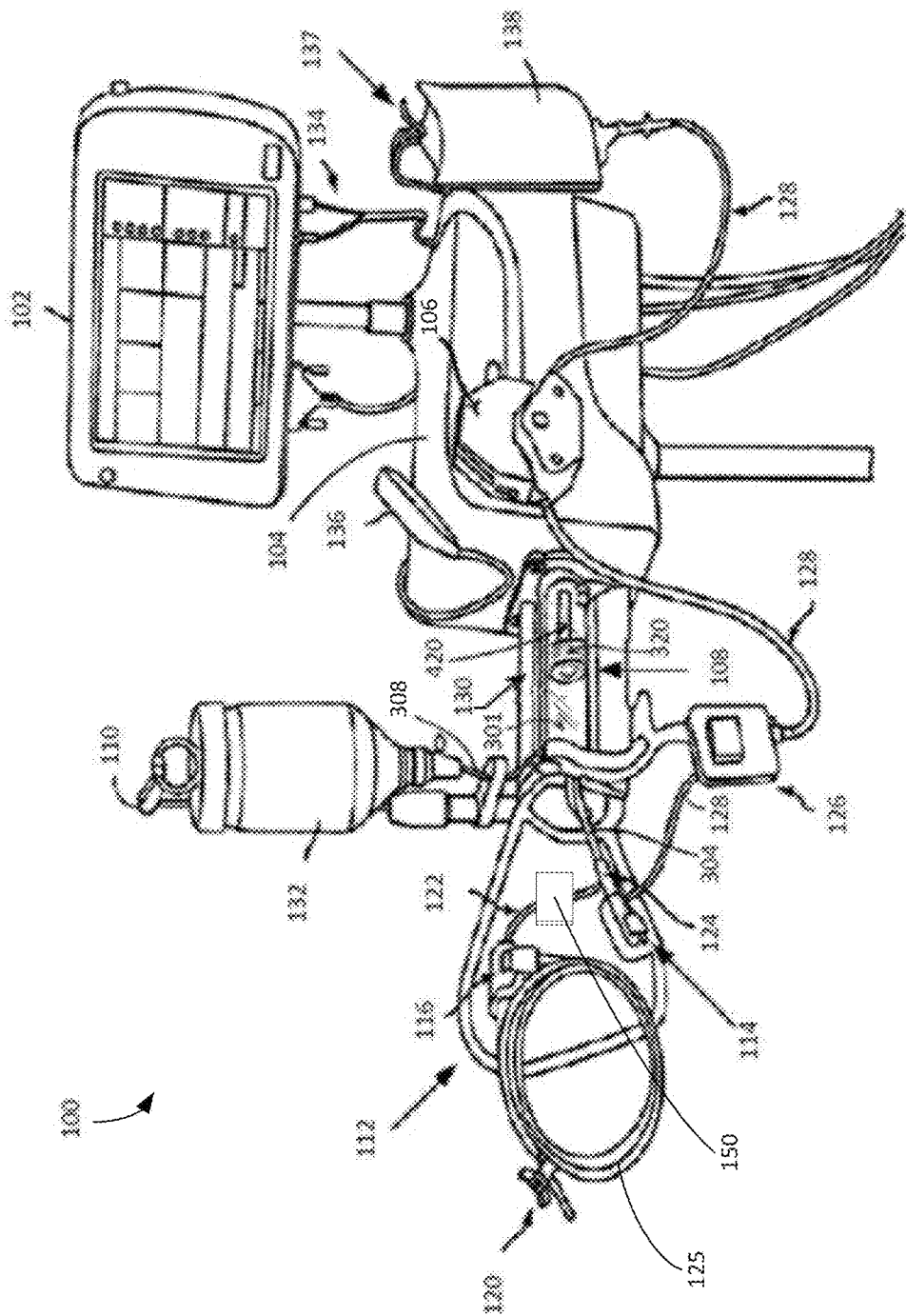
FIG. 1 is a perspective view of an exemplary embodiment of a contrast injector, which can include a sensor protection device.

FIG. 1 is a perspective view of a fluid injection system 100. FIG. 1 illustrates the fluid injection system 100 including a first fluid source 132 and a fluid pressurizing unit 130 mounted in a sleeve 108 that extends from an injector head 104 of the fluid injection system 100. The first fluid source 132 is shown hanging from a holder 110 and being coupled to the fluid pressurizing unit 130, via an input tubing line 308, to supply fluid (e.g., a contrast agent) to the fluid pressurizing unit 130. The fluid pressurizing unit 130 is shown including a reservoir 301 with a plunger shaft 420 extending therein and a plunger 320, which is mounted in the reservoir 301 and coupled to the plunger shaft 420.

According to the illustrated embodiment, the plunger shaft 420 is coupled to a motor assembly contained in the injector head 104, which actuates the plunger shaft 420 to drive the plunger 320 in reciprocating directions within the reservoir 301. The injector head 104 may include a programmable controller array to drive the motor assembly. In some embodiments, the programmable controller array includes a digital computer, which may be programmed, for example, via a control panel 102 of the fluid injection system 100. When the plunger shaft 420 is actuated to move the plunger 320 proximally toward the injector head 104 in a suction stroke, fluid from the first fluid source 132 is drawn into the reservoir 301 via the input tubing line 308. When the plunger shaft 420 moves the plunger 320 distally in a compression stroke, the fluid is expelled out from the reservoir 301 through an output tubing line 304. FIG. 1 further illustrates the output tubing line 304 coupled to a tubing line 122, which is mounted on a module 112 of the fluid injection system 100; the tubing line 122 may be connected to a patient line 125, via a connector 120, so that the fluid, which is expelled from the reservoir 301, is injected into a patient, for example, to facilitate imaging.

With further reference to FIG. 1, the fluid injection system 100 includes a second fluid source 138, which hangs from a hook 137 and from which fluid, for example, a diluent, such as saline, is drawn by a peristaltic pump 106, through a tubing line 128. The peristaltic pump 106 is shown mounted on the injector head 104. The fluid injection system 100 further includes a manifold sensor 114 and a manifold valve 124, for controlling the flow of fluids into the tubing line 122, either from the tubing line 128, or from the fluid pressurizing unit 130 via the output tubing line 304. The manifold valve 124 may comprise a spring-biased spool valve, or another type of valve, for example, a check valve. The manifold sensor 114 can detect the position of manifold valve 124 and report this position to the injector head 104.

A pressure transducer 126 is shown coupled to tubing line 128. When the tubing line 122 is connected to a patient line 125 that extends within a patient, the pressure transducer 126 is capable of functioning as a hemodynamic monitor for the patient. The pressure transducer 126 converts detected pressures into electrical signals that may be monitored or otherwise used by the fluid injection system 100 or another monitoring device.

Similar to the pressure transducer 126, in many embodiments, the fluid injection system 100 may include a pressure sensor assembly 150 coupled to tubing line 122 to measure pressure in the tubing line 122. In some instances, the pressure sensor assembly 150 may measure blood pressure in the tubing line 122 from the patient line 125, for instance, during an angiographic injection procedure. In many instances, the pressure sensor assembly 150 may include a sensor protection device as disclosed elsewhere herein. The pressure sensor assembly 150 can convert detected pressures into electrical signals that may be monitored or otherwise used by the fluid injection system 100 or another monitoring device.

An air bubble detector 116 is shown coupled to the tubing line 122. The air bubble detector 116 is capable of generating an alarm signal, upon detection of a measurable, or otherwise significant, amount of air within the tubing line 122. In addition, the fluid injection system 100 may automatically pause, or terminate, a fluid injection procedure, when the air bubble detector 116 detects air in the tubing.

An operator of the fluid injection system 100, such as a clinician, may use the control panel 102 of the fluid injection system 100 to set up various parameters and/or protocols to be used for a given injection procedure. The operator may interact with the control panel 102, for example, via a touch-screen panel, to enter injection parameters for flow rate, maximum injection volume, maximum injection pressure, rise time, or other parameters. The control panel 102 may further display operating parameters of the fluid injection system 100 to the operator, and/or warning or alarm messages, for example, indicating that air has been detected by the air bubble detector 116.

FIG. 1 also shows a hand control 136 coupled to the control panel 102, via a connector 134, which may be connected to, or disconnected from, the control panel 102. An operator may manipulate the hand control 136 to control injection of fluid from the fluid injection system 100. For example, the operator may use the hand control 136 as a variable-rate control device to variably control the rate of flow of fluid from the fluid injection system 100 (e.g., flow of fluid out of the fluid pressurizing unit 130). The hand control 136 may comprise an electrical device or a pneumatic device.

Because the fluid injection system 100 may deliver many injections over a number of patient procedures, injection fluids may need to be regularly replaced. The injector head 104 may automatically cause the reservoir 301 to be replenished with fluid from the first fluid source 132, for example, based upon monitoring of injection volumes therefrom and comparing to an initial input volume. In some instances, the operator of the fluid injection system 100 may need to manually initiate a fluid replenishment procedure, upon detection that a fluid volume within the reservoir 301 has been depleted to a critical volume. It should be noted that the injector head 104 may automatically initiate replenishment to the reservoir 301 based upon operational state information other than injection volumes. For example, if the injector head 104 determines that the fluid injection system 100 is currently delivering fluid from the peristaltic pump 106, but not from the reservoir 301, and that the reservoir 301 is not filled to capacity, the injector head 104 may cause the motor assembly to actuate the plunger shaft 420 in order to draw additional fluid into the reservoir 301 via the input tubing line 308.

Figure 2:
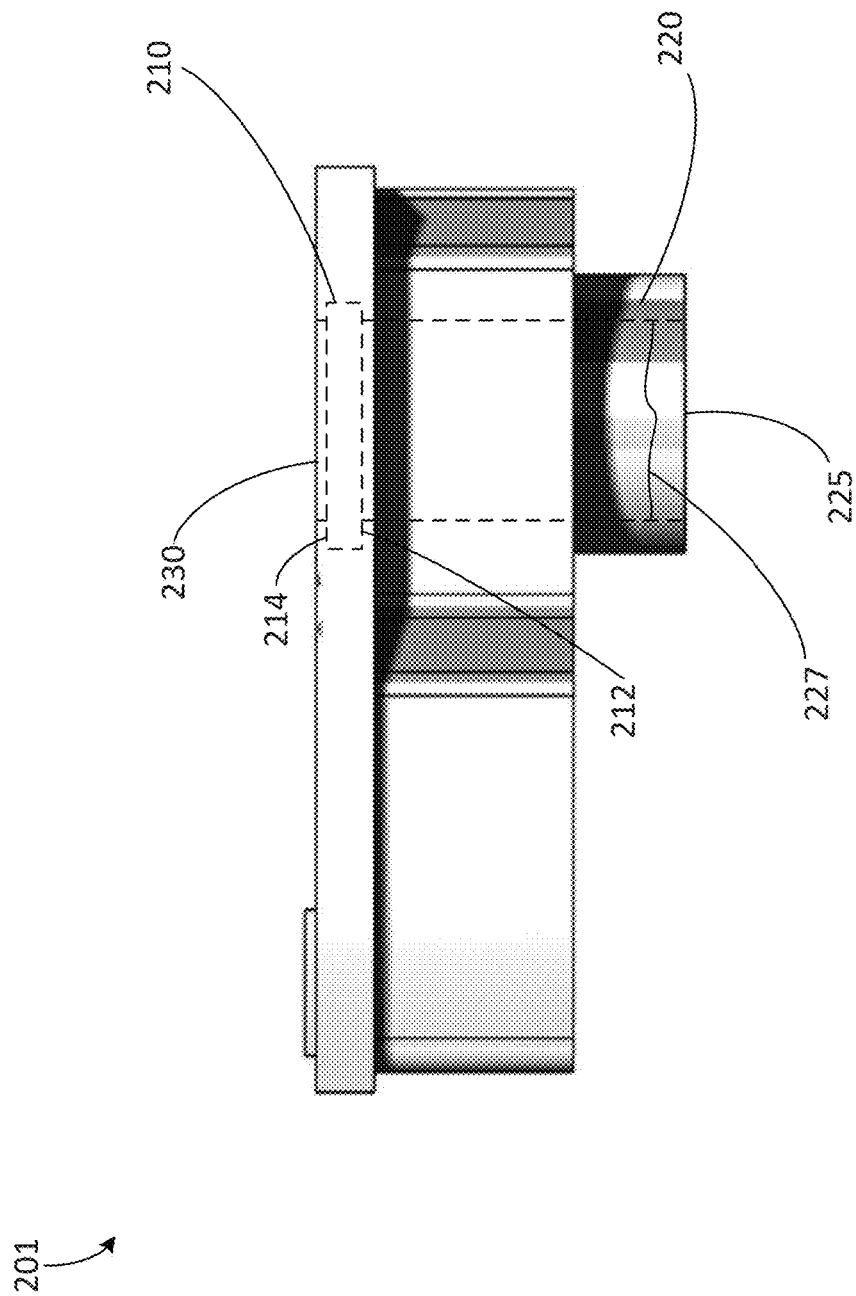
FIG. 2 is a side elevational view of a conventional pressure sensor.

The conventional pressure sensor assembly 201 in FIG. 2, which can be used in as a pressure sensor assembly in a fluid injection system, can include several components that allow it to measure pressure. For instance, the conventional pressure sensor assembly 201 can include a diaphragm 210, a first transfer medium reservoir 220, and an atmospheric gage port 230. The diaphragm 210 may comprise silicon or other suitable material. In many instances, the diaphragm 210 can be positioned between the first transfer medium reservoir 220 and the atmospheric gage port 230. Such positioning of the diaphragm 210 can facilitate pressure measurements.

Components of the conventional pressure sensor assembly 201 can perform pressure measurements by translating pressure to the diaphragm 210 to produce a pressure differential across the diaphragm 210. The first transfer medium reservoir 220 may include a port 225 to interface with the fluid to be measured. The first transfer medium reservoir 220 may be filled with a transfer medium 227 to translate pressure from to-be-measured fluid to a first side 212 of the diaphragm 210. The transfer medium reservoir 220 may comprise thermoplastic (e.g., PC, PVC, etc.). The transfer medium 227 may comprise low durometer (e.g., about 10 amps) fluorosilicone gel. The atmospheric gage port 230 may expose a second side 214 of the diaphragm 210 to atmospheric pressure and, thus, create a pressure differential across the diaphragm 210.

A low-pressure conventional pressure sensor assembly 201 as shown in FIG. 2 can measure blood pressure at low pressures; but can fail if they are used in high pressure applications. In many embodiments, the low-pressure conventional pressure sensor assembly 201 may be a Micro-Electro-Mechanical Systems (MEMS)-based pressure sensor. Using MEMS-based pressure sensors as a conventional pressure sensor assembly 201 for measuring pressure or metrics proportional to pressure is preferable for the compact form factor, versatility, and accuracy of the MEMS pressure sensor. Such sensors can take a variety of forms; but a common form employs a deflectable silicon diaphragm 210 rated for a certain range of pressures coupled with a capacitive or piezoresistive signal transduction. Movement of the medium to be measured is translated to the diaphragm 210, thereby producing in the diaphragm 210 a measurable deflection, or not in instances of zero pressure differential or no flow. As the diaphragm 210 moves, the MEMS-based conventional pressure sensor assembly 201 generates a signal (e.g., an electrical signal) as a function of the deflection imposed on the diaphragm 210. If, however, the pressure, proportional to the deflection, exceeds the pressure rating and a predetermined failure threshold (e.g., the overpressure rating), the diaphragm 210 will rupture and become unusable.

A pressure sensor protection device 300 as shown in FIGS. 3-8 positioned to measure fluid flow pressure during an injection procedure may be subjected to high and low pressures. In many instances, the sensor protection device 300 can be located between the injector and the patient. For example, the sensor protection device 300 can be placed in the pumping line, which may receive high-pressure injection fluid, low-pressure blood, or both. Thus, positioning the sensor protection device 300 in the pumping line may enable the pressure sensor assembly 341 to measure blood pressure when contrast media is not being injected and to be exposed to the high-pressure contrast media during injection without being damaged.

Figure 3:
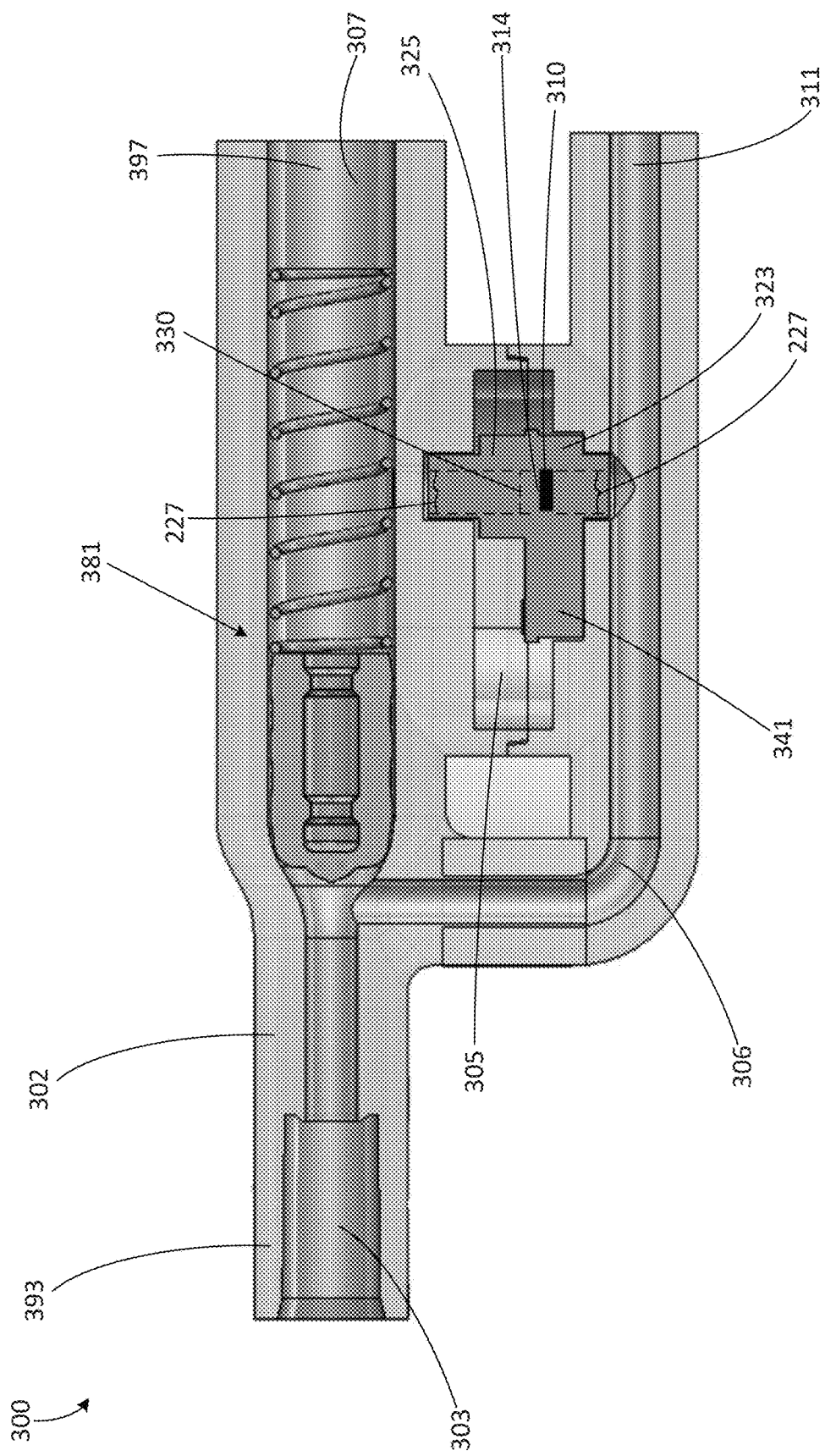
FIG. 3 is a side elevational cross-sectional view of an illustrative pressure sensor protection device with a plunger in a plunger closed position.

An illustrative sensor protection device 300 shown in FIG. 3 may protect conventional low-pressure blood pressure sensors in high-pressure fluid flow applications. The sensor protection device 300 may include a pressure sensor assembly 341, a sensor protection housing 302, and a plunger assembly 381. During low pressure, the sensor protection device 300 can allow a pressure differential across components of the pressure sensor assembly 341 to measure pressure. In contrast, during high-pressure fluid flow, the sensor protection device 300 may not allow a pressure differential across components of the pressure sensor assembly 341, e.g., by placing the pressure sensor assembly 341 in equilibrium. Thus, the sensor protection device 300 can allow use of conventional blood pressure measurement techniques and devices while limiting risks of the pressure sensor assembly 341 failing during high-pressure fluid flow applications.

The pressure sensor assembly 341 may be similar to a conventional pressure sensor with a pressure sensor housing that includes a first transfer medium reservoir 323 and that may also include a second transfer medium reservoir 325. The second transfer medium reservoir 325 can be positioned over the second sensor port (e.g., atmospheric gage port) 330. A transfer medium 227 may fill the second transfer medium reservoir 325 and translate pressure from fluid to a second side 314 of the diaphragm 310. The pressure sensor assembly 341 may comprise ceramic substrate. The fluid transfer medium 227 may comprise low durometer (e.g., about 10 amps) fluorosilicone gel. Fluid to be measured can be introduced to the pressure sensor assembly 341 through the sensor protection housing 302.

The sensor protection device 300 may include a sensor protection housing 302, which can route fluid to the pressure sensor assembly 341. The sensor protection housing 302 may include an inlet 303, an outlet 311, a sensor chamber 305, a primary flow path 306, and a secondary flow path 307. The inlet 303 may be at the proximal end 393 of the sensor protection housing 302. The outlet 311 may be at the distal end 397 of the sensor protection housing 302. The sensor protection housing 302 in many embodiments can comprise molded or machined thermoplastic (e.g., polycarbonate, PVC, PSU, etc.).

Figure 4:
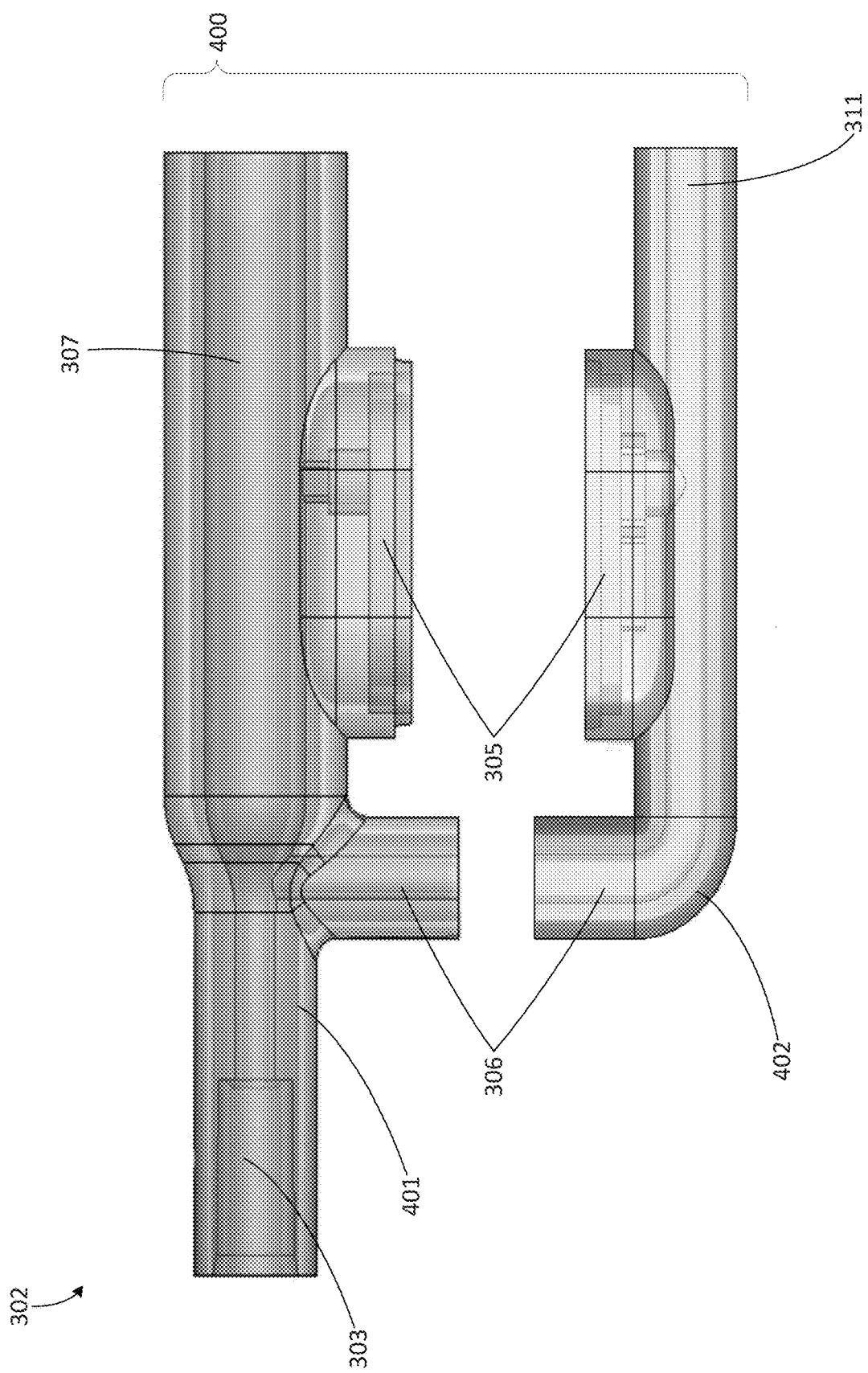
FIG. 4 is a side elevational exploded view of a first complementary housing segment and a second complementary housing segment.

As shown in FIG. 4, in some embodiments, the sensor protection housing 302 may be composed of complementary segments 400. In many embodiments, the complementary segments 400 of the sensor protection housing 302 shown in FIG. 4 may include one or more components or portions of components of the sensor protection housing 302. For instance, a first complementary segment 401 may include the inlet 303 and the secondary flow path 307. A second complementary segment 402 may include the outlet 311. In some instances, one or more components of the sensor protection housing 302 (e.g., the sensor chamber 305 and the primary flow path 306) may be formed between mating sections (e.g., one or more) in the complementary segments 400.

Figure 5:
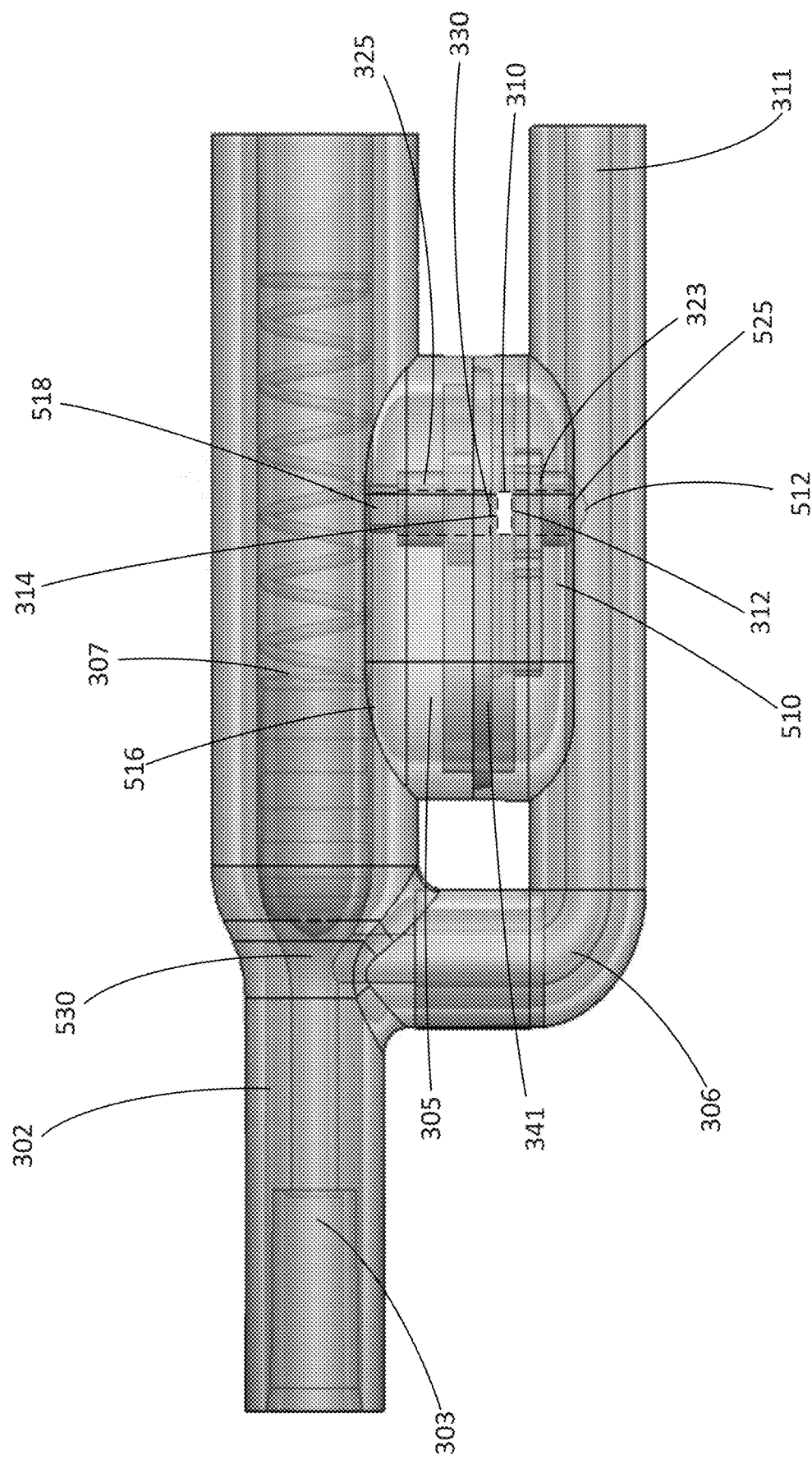
FIG. 5 is a side elevational view of an illustrative pressure sensor protection device assembled together with the first and second complementary housing segments.

The sensor chamber 305 shown in FIG. 5 may contain the pressure sensor assembly 341 and be exposed to fluid from other components of the sensor protection housing 302. The sensor chamber 305 can have a first chamber port 512 on a first side 510 that aligns with a first sensor port 525 in the in the first transfer medium reservoir 323. In such instances, the first chamber port 512 on the first side 510 can expose the first side 312 of the diaphragm 310 to pressure from fluid in the primary flow path 306 (e.g., both high pressure and low pressure fluid). A second chamber port 518 on a second side 516 may align with the second sensor port 330 in the second transfer medium reservoir 325. In such instances, the second chamber port 518 in the second side 516 can expose the second side 314 of the diaphragm 310 to atmospheric pressure or to pressure from high pressure fluid.

Both high-pressure and low-pressure fluid may enter and exit the sensor protection housing 302 through the primary flow path 306. The primary flow path 306 may receive fluid from the inlet 303 in the sensor protection housing 302. The primary flow path 306 may feed fluid into the first side 510 of the sensor chamber 305 through the first chamber port 512 in the primary flow path 306. The primary flow path 306 may expel fluid through the outlet 311 in the sensor protection housing 302.

High-pressure fluid, but not low-pressure fluid, may enter the secondary flow path 307 without leaving the sensor protection housing 302. The secondary flow path 307 may form a junction 530 with the primary flow path 306. The secondary flow path 307 may feed high-pressure fluid into the second side 516 of the sensor chamber 305 through a second chamber port 518 in the secondary flow path 307.

Figure 6:
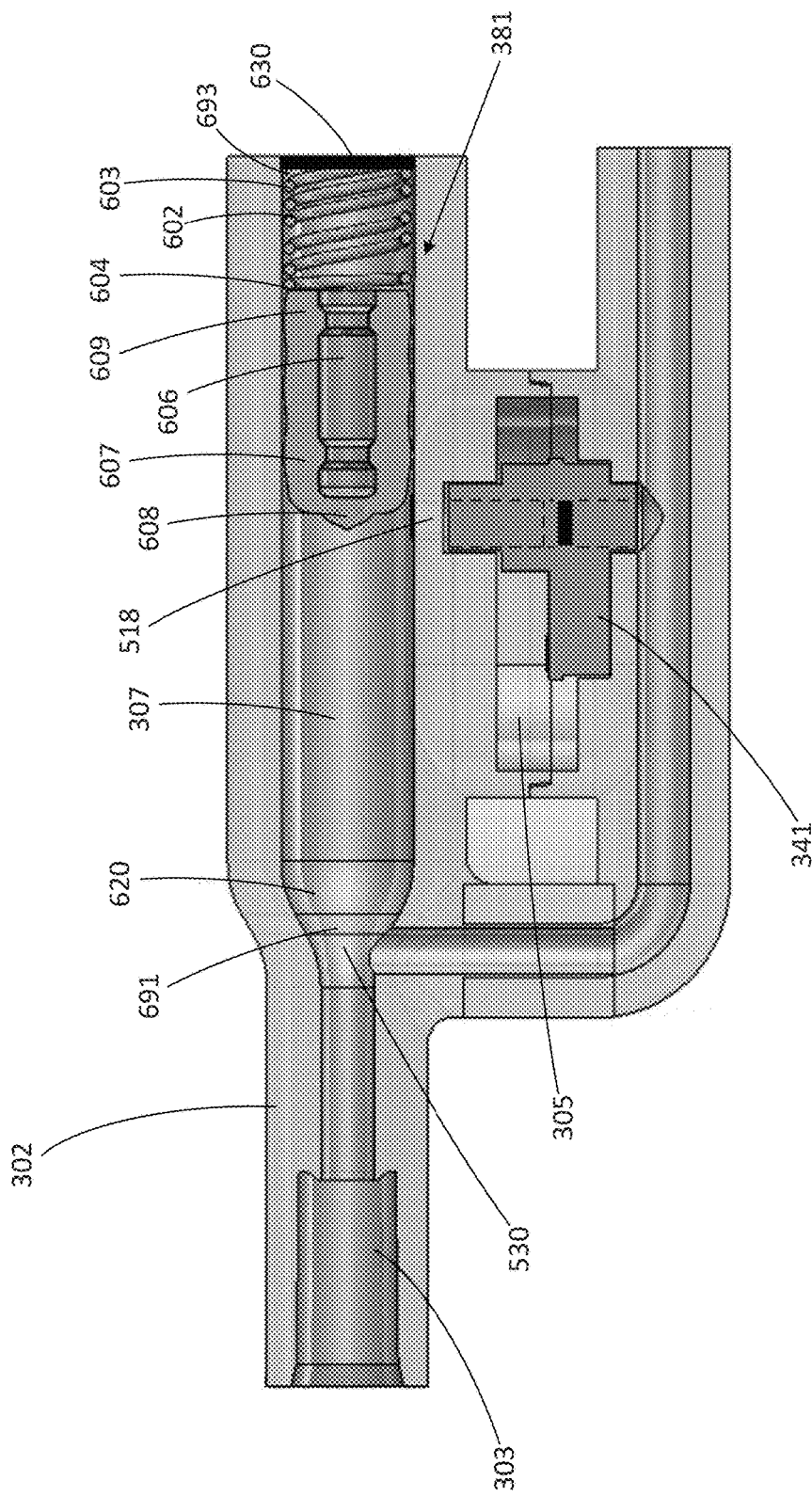
FIG. 6 is a side elevational cross-sectional view of an illustrative pressure sensor protection device with the plunger in a plunger open position.

The plunger assembly 381 shown in FIG. 6 may be exposed to high-pressure fluid flow in the sensor protection housing 302. The plunger assembly 381 in the sensor protection device 300 may include an axial biasing member 602, a core 606, and a plunger 607. In many instances, the components of the plunger assembly 381 can be connected together. The plunger assembly 381 can be contained within the sensor protection housing 302 and exposed to fluid flow.

The plunger assembly 381 may be positioned within the sensor protection housing 302 opposite fluid flow from the inlet 303. The plunger assembly 381 may be in the secondary flow path 307 of the sensor protection housing 302. The plunger 607 may be positioned in the secondary flow path 307 between a plunger seat 620 and a plunger stop 630. The plunger seat 620 may be located at a proximal end 691 of the secondary flow path 307 near the junction 530. The plunger stop 630 may be located at a distal end 693 of the secondary flow path 307. In some embodiments, the plunger assembly 381 may be fully extended (e.g., under zero compression) and free to move within the secondary flow path 307.

The plunger assembly 381 can travel within the sensor protection housing 302 along the secondary flow path 307. The axial biasing member 602 can have a first end 603 near the plunger stop 630. The axial biasing member 602 in many instances can be a compression spring (e.g., a coil spring) and comprise metal (e.g., stainless steel). The core 606 can connect to the axial biasing member 602, for instance, at a second end 604 of the axial biasing member 602 opposite the first end 603 of the axial biasing member 602. Movement of the plunger assembly 381 within the secondary flow path 307 can be limited in the distal direction by the plunger stop 630 and limited in the proximal direction of the sensor protection housing 302 by the plunger seat 620. Thus, the plunger assembly 381 can move within the secondary flow path 307 between the plunger stop 630 and the plunger seat 620.

Movement of the plunger assembly 381 may, depending on fluid flow or the pressure of the fluid, allow fluid to access the second chamber port 518 in the sensor chamber 305 of the pressure sensor assembly 341 without leaving the sensor protection housing 302. An illustrative plunger 607 can be built on top of the core 606. The plunger 607 can have a fit tightly within the secondary flow path 307. A leading end 608 of the plunger 607 can be in the plunger seat 620 at low pressures and clear of the second chamber port 518 in the sensor chamber 305 during high pressures. The trailing end 609 of the plunger 607 can be near the axial biasing member 602. The plunger 607 may comprise molded elastomer or vulcanized rubber product (e.g., TPV, TPU, TPE, Silicone, etc.) or vulcanized synthetic rubber (e.g., isoprene, EPDM, etc.).

Figure 7:
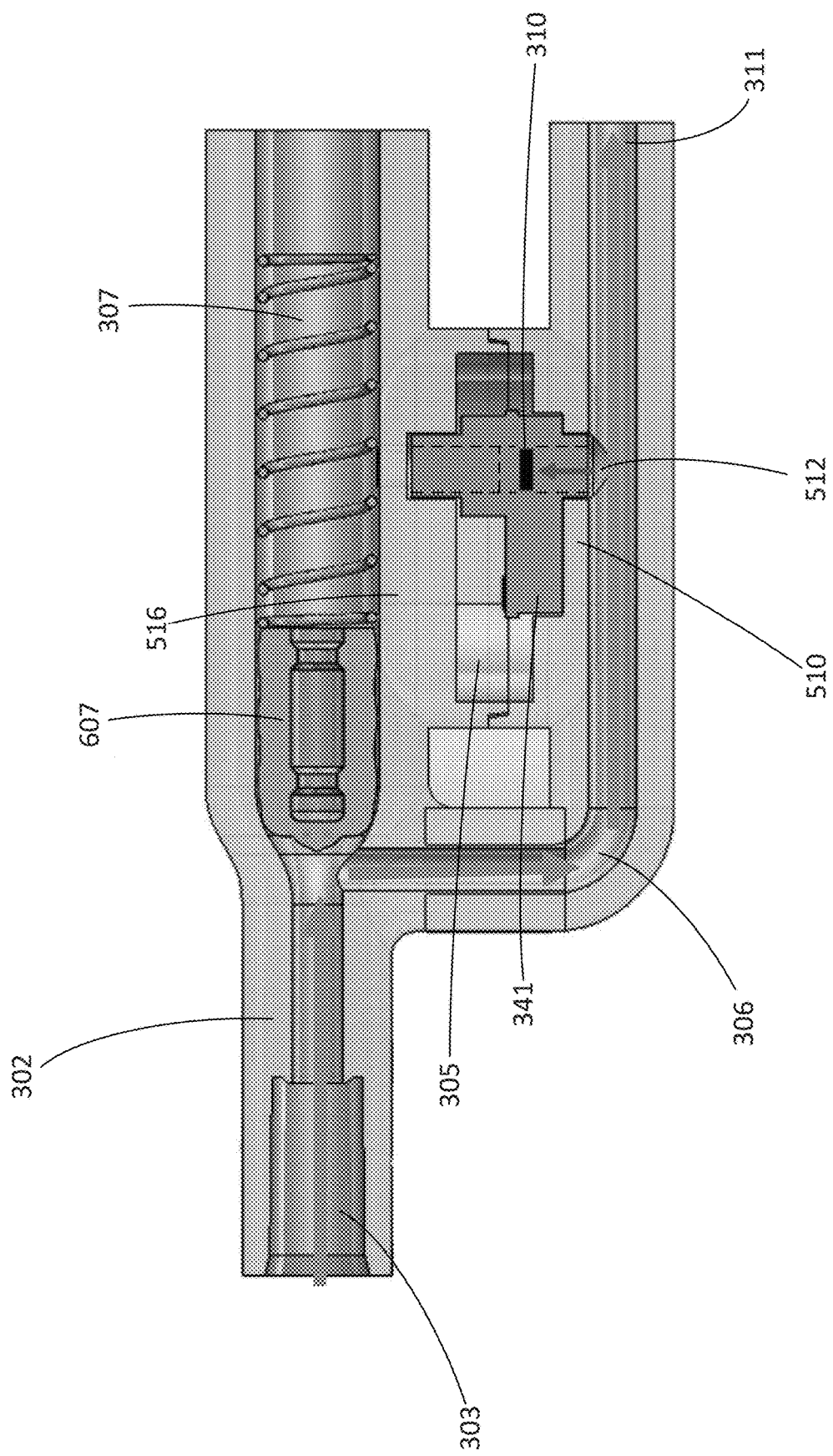
FIG. 7 is a side elevational cutaway view of a fluid flow path in an illustrative pressure sensor protection device with the plunger in the plunger closed position and with arrows indicating a fluid flow path.
Figure 8:
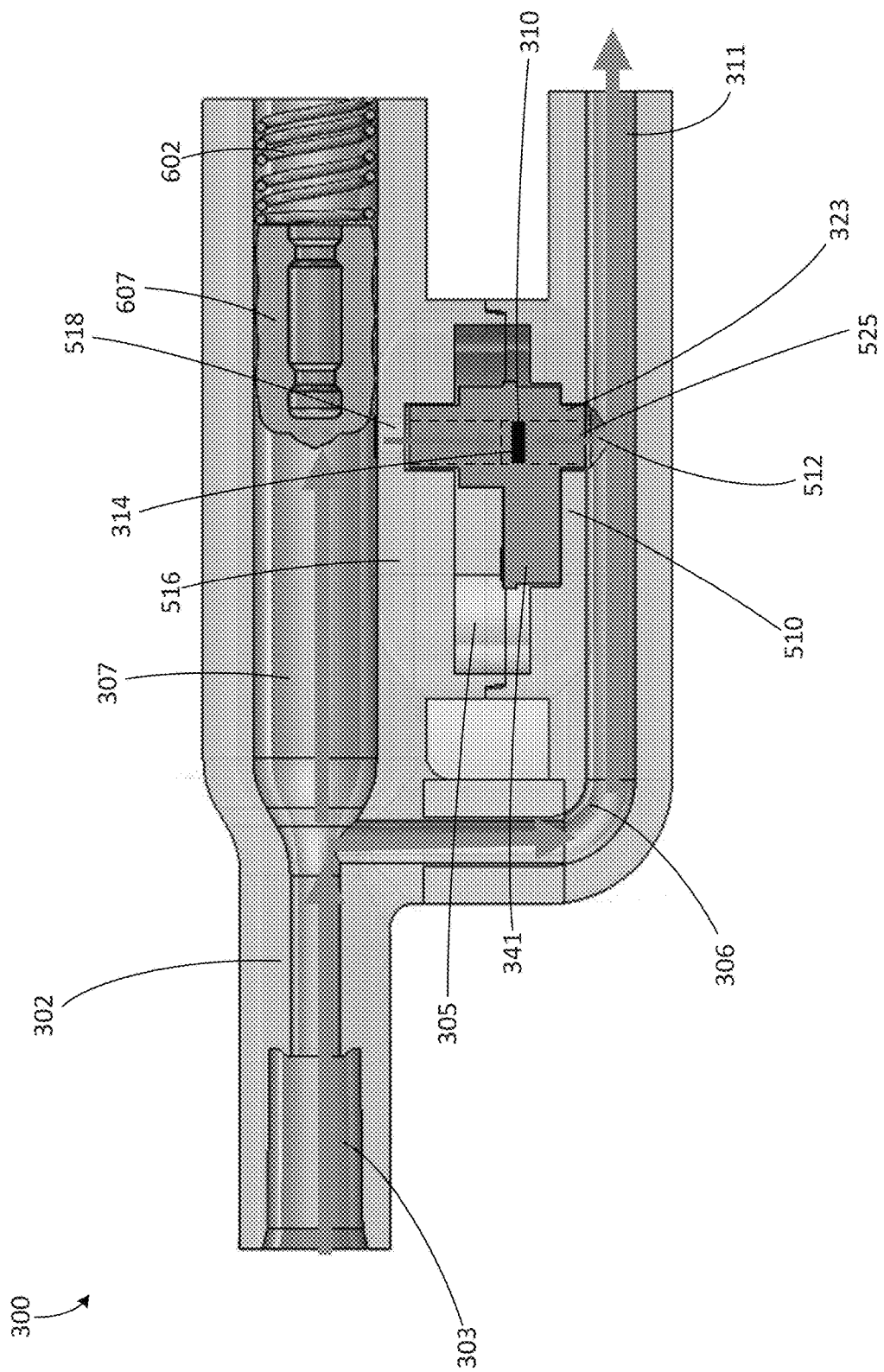
FIG. 8 is a side elevational cutaway view of a fluid flow path in an illustrative pressure sensor protection device with the plunger in the plunger open position and with arrows indicating a fluid flow path.

The plunger 607 can be configured to move between a plunger closed position and a plunger open position as seen in FIGS. 7 and 8. For example, during low pressure, the plunger 607 can be in the plunger closed position as shown in FIG. 7. Thus, fluid flows into the sensor protection housing 302 through the inlet 303 in the sensor protection housing 302, through the primary flow path 306, into the first side 510 of the sensor chamber 305 through the first chamber port 512, and out of the sensor protection housing 302 through the outlet 311 in the sensor protection housing 302. In such a position, the plunger 607 prevents fluid from flowing into the secondary flow path 307 such that fluid cannot enter the second side 516 of the sensor chamber 305. In such a position, the plunger 607 can seal the secondary flow path 307 to prevent fluid from flowing past the plunger 607. Instead, the second side 516 of the sensor chamber 305 can be exposed to atmospheric pressure, thereby creating a pressure differential across the diaphragm 310. In some such circumstances, to establish a pressure measurement, the pressure sensor assembly 341 can measure the pressure differential between fluid pressure on the first side 510 of the sensor chamber 305 and the atmospheric pressure on second side 516 of the sensor chamber 305.

In many embodiments, the plunger 607 can move from the plunger closed position of FIG. 7 to the plunger open position of FIG. 8 as fluid flow transitions from low pressure to high pressure. As pressure rises above a predetermined value, the plunger 607 is pushed into the plunger open position, thereby compressing the axial biasing member 602. In such instances, fluid can flow into the sensor protection housing 302 through the inlet 303 in the sensor protection housing 302, through the primary flow path 306, into the first side 510 of the sensor chamber 305 through the first chamber port 512, and out of the sensor protection housing 302 through the outlet 311 in the sensor protection housing 302. In such instances, fluid may also flow through the secondary flow path 307 into the second side 516 of the sensor chamber 305 through the second chamber port 518. Thus, the first and second sides 510, 516 of the sensor chamber 305 can be exposed to same pressure from high-pressure fluid, protecting the diaphragm 310.

Many embodiments may have the plunger 607 transition back to the low-pressure configuration by itself with little or no direct operator intervention. As pressure drops back below the predetermined value, the axial biasing member 602 pushes the plunger 607 back into the plunger closed position. Fluid can flow through the primary flow path 306, and the pressure sensor assembly 341 can measure the differential of fluid pressure from atmospheric pressure across the diaphragm 310.

The predetermined value at which the axial biasing member 602 causes the plunger 607 to move can be selected based on various factors such as the pressure sensor assembly's failure threshold and a desired system response time. The predetermined value may be selected to be lower than the pressure sensor assembly's failure threshold. For example, if the pressure sensor assembly's failure threshold is 100-200 psi, a predetermined value of 60 psi may be selected. For pressure sensor assemblies with higher failure thresholds (e.g., 1,200 psi), a higher predetermined value (e.g., 1,000 psi) may be selected. In many embodiments, the predetermined value may be between 500 psi and 700 psi (e.g., 600 psi). The selected predetermined value may be implemented through choice of axial biasing member 602 and, in some cases, degree of friction between the plunger 607 and the secondary flow path 307. As noted, the desired system response time may factor into selection of the predetermined value. Choosing a predetermined value that is lower than, but relatively close to, the pressure sensor assembly's failure threshold may ensure that the plunger 607 moves fully back to the plunger closed position when high-pressure injection is complete and may allow the pressure sensor assembly to begin sensing pressure soon after high-pressure injection is complete.

Although operation has been discussed primarily in conjunction with injections, one skilled in the art that the sensor protection device 300 may be used in a variety of different applications. For instance, the sensor protection device 300 can be used to protect low-pressure sensors with an operating fluid other than blood. For example, some such fluids may include saline.

An illustrative method for protecting low pressure sensors in high-pressure applications is also disclosed. The method can include providing a sensor protection device. The sensor protection device can be similar to those disclosed elsewhere herein. In some embodiments, the high-pressure application is an injection system as disclosed elsewhere herein. The method can include supplying fluid to the sensor protection device from a high-pressure system through a fluid line. If the fluid in the fluid line is at high pressure, the valve in the secondary flow path will open to allow fluid from the primary flow path into the secondary flow path, thereby placing the pressure sensor assembly in equilibrium. If the fluid in the fluid line is at low pressure, the valve in the secondary flow path will be closed, and the pressure of the fluid in the primary fluid line can be measured versus atmospheric pressure.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A sensor protection device comprising:
   (a) a pressure sensor assembly, the pressure sensor assembly including (i) a diaphragm with first and second sides and (ii) a pressure sensor housing that houses the diaphragm and that comprises a first sensor port configured to enable fluid to press against the first side of the diaphragm and a second sensor port configured to enable fluid to press against the second side of the diaphragm;
   (b) a sensor protection housing that includes (i) an inlet, (ii) an outlet, (iii) a sensor chamber that houses the pressure sensor assembly and that includes a first chamber port aligned with the first sensor port and a second chamber port aligned with the second sensor port, (iv) a primary flow path from the inlet to the outlet that enables fluid to flow through the first chamber port and the first sensor port, and (v) a secondary flow path that enables fluid to flow through the second chamber port and the second sensor port; and
   (c) a plunger assembly positioned in the secondary flow path and including (i) a plunger and (ii) an axial biasing member configured to position the plunger in a plunger closed position when a pressure of fluid within the sensor protection housing is below a predetermined value and in a plunger open position when the pressure of fluid within the sensor protection housing is above the predetermined value, the plunger preventing fluid from flowing through the second chamber port and the second sensor port when in the plunger closed position and permitting fluid to flow through the second chamber port and the second sensor port when in the plunger open position.

2. The sensor protection device of claim 1, wherein fluid pressed against the first side of the diaphragm and fluid pressed against the second side of the diaphragm are at equal pressure when the plunger is in the plunger open position.

3. The sensor protection device of claim 1, wherein the second side of the diaphragm is exposed to atmospheric pressure when the plunger is in the plunger closed position.

4. The sensor protection device of claim 1, wherein the predetermined value is a value between 60 pounds per square inch (psi) and 1,000 psi.

5. The sensor protection device of claim 1, wherein the pressure sensor housing comprises:
   a first transfer medium reservoir positioned over the first sensor port, the first transfer medium reservoir being filled with a first transfer medium to translate pressure from the fluid within the sensor protection housing to the first side of the diaphragm; and
   a second transfer medium reservoir positioned over the second sensor port, the second transfer medium reservoir being filled with a second transfer medium to translate pressure from the fluid within the sensor protection housing to the second side of the diaphragm.

6. The sensor protection device of claim 5, wherein the first transfer medium and the second transfer medium each comprise fluorosilicone gel.

7. The sensor protection device of claim 1, wherein the plunger comprises molded elastomer or vulcanized rubber product or vulcanized synthetic rubber, and the plunger seals the secondary flow path to prevent fluid from flowing past the plunger.

8. The sensor protection device of claim 1, wherein the axial biasing member comprises a compression spring.

9. A method of protecting a pressure sensor, comprising:
   (a) providing a sensor protection housing that includes (i) an inlet, (ii) an outlet, (iii) a sensor chamber that includes a first chamber port and a second chamber port, (iv) a primary flow path from the inlet to the outlet, and (v) a secondary flow path;

(b) providing a plunger assembly positioned in the secondary flow path of the sensor protection housing, the plunger assembly including (i) a plunger and (ii) an axial biasing member;

(c) inserting a pressure sensor assembly into the sensor chamber of the sensor protection housing, the pressure sensor assembly including (i) a diaphragm with first and second sides and (ii) a pressure sensor housing that houses the diaphragm and that comprises a first sensor port configured to enable fluid to press against the first side of the diaphragm and a second sensor port configured to enable fluid to press against the second side of the diaphragm, wherein inserting the pressure sensor assembly into the sensor chamber comprises aligning the first sensor port with the first chamber port and aligning the second sensor port with the second chamber port;

(d) flowing fluid into the sensor protection housing through the inlet at a fluid pressure, wherein (i) fluid flows along the primary flow path and out the outlet and flows through the first chamber port and the first sensor port, (ii) fluid flows along the secondary flow path through the second chamber port and the second sensor port if the fluid pressure is above a predetermined value, and (iii) the plunger prevents fluid from flowing along the secondary flow path through the second chamber port and the second sensor port if the fluid pressure is below the predetermined value.

10. The method of claim 9, wherein the sensor protection housing is composed of first and second complementary segments, and wherein inserting the pressure sensor assembly into the sensor chamber of the sensor protection housing includes mating the first and second complementary segments together by one or more mating sections.

11. The method of claim 10, wherein the first complementary segment includes the inlet and the secondary flow path, the second complementary segment includes the outlet, and wherein the sensor chamber and the primary flow path are formed between the one or more mating sections.

12. The method of claim 9, wherein fluid pressed against the first side of the diaphragm and fluid pressed against the second side of the diaphragm are at equal pressure when the fluid pressure is above the predetermined value.

13. The method of claim 9, wherein the second side of the diaphragm is exposed to atmospheric pressure when the fluid pressure is below the predetermined value.

14. The method of claim 9, wherein the predetermined value is a value between 60 pounds per square inch (psi) and 1,000 psi.

15. The method of claim 9, wherein the pressure sensor housing comprises:

a first transfer medium reservoir positioned over the first sensor port, the first transfer medium reservoir being filled with a first transfer medium to translate pressure from the fluid within the sensor protection housing to the first side of the diaphragm; and a second transfer medium reservoir positioned over the second sensor port, the second transfer medium reservoir being filled with a second transfer medium to translate pressure from the fluid within the sensor protection housing to the second side of the diaphragm.

16. The method of claim 15, wherein the first transfer medium and the second transfer medium each comprise fluorosilicone gel.

17. The method of claim 9, wherein the plunger comprises molded elastomer or vulcanized rubber product or vulcanized synthetic rubber, and the plunger seals the secondary flow path to prevent fluid from flowing past the plunger.

18. The method of claim 9, wherein the axial biasing member comprises a compression spring.

19. A sensor protection device comprising:

(a) a sensor protection housing that includes (i) an inlet, (ii) an outlet, (iii) a sensor chamber that includes first and second chamber ports;

(b) a pressure sensor assembly including a diaphragm with first and second sides and a pressure sensor housing that houses the diaphragm and that comprises a first sensor port configured to enable fluid to press against the first side of the diaphragm and a second sensor port configured to enable fluid to press against the second side of the diaphragm, wherein the first chamber port is configured to be aligned with the first sensor port and the second chamber port is configured to be aligned with the second sensor port, (iv) a primary flow path from the inlet to the outlet that enables fluid to flow through the first chamber port and the first sensor port, and (v) a secondary flow path that enables fluid to flow through the second chamber port and the second sensor port; and (c) a plunger assembly positioned in the secondary flow path and including (i) a plunger and (ii) an axial biasing member configured to position the plunger in a plunger closed position when a pressure of fluid within the sensor protection housing is below a predetermined value and in a plunger open position when the pressure of fluid within the sensor protection housing is above the predetermined value, the plunger preventing fluid from flowing through the second chamber port and the second sensor port when in the plunger closed position and permitting fluid to flow through the second chamber port and the second sensor port when in the plunger open position.

20. The sensor protection device of claim 19, wherein the predetermined value is a value between 60 pounds per square inch (psi) and 1,000 psi.

* * * * *